United States Patent
Yamada et al.

(10) Patent No.: US 10,253,343 B2
(45) Date of Patent: Apr. 9, 2019

(54) METHOD OF PRODUCING SUGAR SOLUTION AND XYLOOLIGOSACCHARIDE

(71) Applicant: Toray Industries, Inc., Tokyo (JP)

(72) Inventors: Chiaki Yamada, Kamakura (JP);
Hiroyuki Kurihara, Kamakura (JP);
Katsushige Yamada, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 15/521,990

(22) PCT Filed: Oct. 29, 2015

(86) PCT No.: PCT/JP2015/080490
§ 371 (c)(1),
(2) Date: Apr. 26, 2017

(87) PCT Pub. No.: WO2016/068223
PCT Pub. Date: May 6, 2016

(65) Prior Publication Data
US 2017/0314051 A1    Nov. 2, 2017

(30) Foreign Application Priority Data
Oct. 31, 2014  (JP) .................. 2014-222968

(51) Int. Cl.
*C12P 19/02* (2006.01)
*C12P 19/12* (2006.01)
*C12P 19/14* (2006.01)

(52) U.S. Cl.
CPC .............. *C12P 19/14* (2013.01); *C12P 19/02* (2013.01); *C12P 19/12* (2013.01); *C12Y 302/01004* (2013.01); *C12Y 302/01008* (2013.01)

(58) Field of Classification Search
None
See application file for complete search history.

(56) References Cited

U.S. PATENT DOCUMENTS

| 2002/0174962 A1 | 11/2002 | Izumi et al. |
| 2013/0157318 A1 | 6/2013 | Ishikawa et al. |
| 2013/0203117 A1 | 8/2013 | Kurihara et al. |
| 2015/0125908 A1 | 5/2015 | Kurihara et al. |

FOREIGN PATENT DOCUMENTS

| JP | 61-242592 A | 10/1986 |
| JP | 3951545 B2 | 8/2007 |
| JP | 4557648 B2 | 10/2010 |
| JP | 4947223 B1 | 6/2012 |
| WO | 2011/115040 A1 | 9/2011 |
| WO | 2013/172446 A1 | 11/2013 |

OTHER PUBLICATIONS

Ishihara, M. et al., "Semicontinuous enzymatic hydrolysis of lignocelluloses", *Biotechnol. Bioeng.*, 1991, vol. 37, pp. 948-954, Abstract only.

*Primary Examiner* — Iqbal H Chowdhury
(74) *Attorney, Agent, or Firm* — DLA Piper LLP (US)

(57) ABSTRACT

A method of producing a sugar liquid and a xylooligosaccharide includes Steps (1) to (3): Step (1): hydrolyzing a cellulose-containing biomass with a filamentous fungus-derived cellulase; Step (2): subjecting the hydrolysate of Step (1) to solid-liquid separation, and filtering the solution component through an ultrafiltration membrane to recover cellulase as a non-permeate, and to recover a sugar liquid as a permeate; and Step (3): reacting the recovered cellulase in Step (2) with a xylan-containing material, and recovering a xylooligosaccharide produced, Step (3) being independent from Step (1).

11 Claims, 1 Drawing Sheet

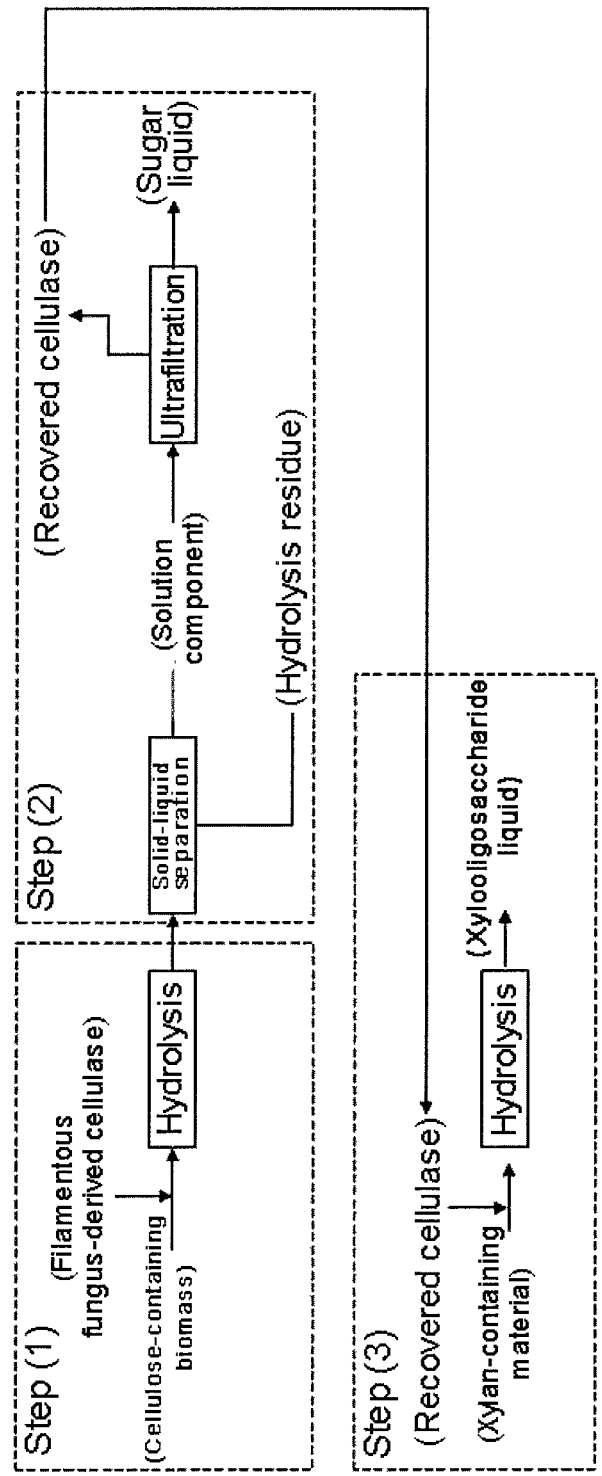

METHOD OF PRODUCING SUGAR SOLUTION AND XYLOOLIGOSACCHARIDE

TECHNICAL FIELD

This disclosure relates to a method of producing a sugar liquid and a xylooligosaccharide from a cellulose-containing biomass.

BACKGROUND

The process of fermentation production of a chemical product using a sugar as a raw material is utilized for production of various industrial materials. In recent years, production processes for sugars using cellulose-containing biomass that does not compete with food have been widely studied. In particular, methods using cellulase are attracting attention since such methods use less energy and cause less environmental load, while achieving high sugar yields.

Oligosaccharides have low sweetness and low calorie contents, and hardly cause dental caries. Since they have an effect of selectively promoting the growth of intestinal bacteria, a number of products are commercially available as, for example, foods for specified health uses having a function to keep favorable stomach conditions. Among these oligosaccharides, xylooligosaccharides are less susceptible to degradation by acids or digestive enzymes such as amylase and, when they are ingested by humans, they are not degraded or absorbed until they reach the large intestine. Thus, they produce their effect with a minimum effective amount of 0.2 to 0.7 g/day (Japan Confectionery and Innovative Food Ingredients Research Center; Handbook of Oligosaccharides), which is an order of magnitude smaller than those of other oligosaccharides. Xylooligosaccharides are used not only as food for humans, but also as an additive for livestock feed.

Xylooligosaccharides are produced from xylan, which is one of major constituting components of plants. Known examples of methods of producing xylooligosaccharides include a method in which pulverized hardwood is placed in circulated high temperature/high pressure water to allow hydrolytic extraction of hemicellulose in the material (JP 4557648 B), a method in which xylan is treated with xylanase produced by a *Bacillus* microorganism, and xylooligosaccharide is produced from the reaction filtrate (JP 61-242592 A), and a method in which a xylooligosaccharide complex contained in the reaction filtrate obtained after reaction of a chemical pulp with hemicellulase is concentrated by membrane filtration, and xylooligosaccharides are separated and recovered from the resulting concentrate (JP 3951545 B).

Xylanase is a representative enzyme used for production of xylooligosaccharides. Cellulases produced by microorganisms represented by filamentous fungi such as the genera *Trichoderma, Acremonium, Streptomyces,* and *Aspergillus* are known to have xylanase activity. On the other hand, those cellulases are known to have also β-xylosidase activity, which causes degradation of xylooligosaccharides into monosaccharide units. Thus, efficient production of xylooligosaccharides requires removal of β-xylosidase by purification of xylanase from cellulase produced by a microorganism, production of xylanase using a microorganism which does not produce β-xylosidase or the like to eliminate the influence of β-xylosidase. However, any of those methods leads to an increase in the cost of the enzyme.

As described above, xylanase is used for production of xylooligosaccharides using an enzyme. However, when cellulase having xylanase activity is used, the cellulase has not only the xylanase activity, but also β-xylosidase activity, which causes degradation of xylooligosaccharides. It has therefore been difficult to produce xylooligosaccharides using cellulase.

In view of this, it could be helpful to construct a process for simultaneous production of a sugar liquid and a xylooligosaccharide using cellulase to reduce the amount of enzyme used in the entire production process of the sugar liquid and the xylooligosaccharide, which are valuable substances, compared to the amount of enzyme used in conventional production processes in which a sugar liquid and a xylooligosaccharide are produced using separate enzymes.

SUMMARY

We discovered that, after hydrolyzing cellulose-containing biomass with a filamentous fungus-derived cellulase, cellulase recovered from the resulting hydrolysate can be used for production of xylooligosaccharide.

We thus provide:

[1] A method of producing a sugar liquid and a xylooligosaccharide, comprising the following Steps (1) to (3):
Step (1): a step of hydrolyzing a cellulose-containing biomass with a filamentous fungus-derived cellulase;
Step (2): a step of subjecting the hydrolysate of Step (1) to solid-liquid separation, and filtering the solution component through an ultrafiltration membrane to recover cellulase as a non-permeate, and to recover a sugar liquid as a permeate; and
Step (3): a step of reacting the recovered cellulase in Step (2) with a xylan-containing material, and recovering a xylooligosaccharide produced.

[2] The method of producing a sugar liquid and a xylooligosaccharide according to [1], wherein the filamentous fungus-derived cellulase is *Trichoderma reesei*-derived cellulase.

[3] The method of producing a sugar liquid and a xylooligosaccharide according to [1] or [2], wherein, in Step (2), the electric conductivity of the hydrolysate in Step (1) is less than 16 mS/cm.

[4] The method of producing a sugar liquid and a xylooligosaccharide according to any one of [1] to [3], wherein the β-xylosidase activity of the recovered cellulase in Step (2) is less than 5% of that of the filamentous fungus-derived cellulase used in Step (1).

[5] The method of producing a sugar liquid and a xylooligosaccharide according to any one of [1] to [4], wherein the recovered cellulase in Step (2) contains at least xylanase.

[6] The method of producing a sugar liquid and a xylooligosaccharide according to any one of [1] to [5], wherein Step (1) is a step of hydrolyzing a pretreated product of the cellulose-containing biomass with the filamentous fungus-derived cellulase.

[7] The method of producing a sugar liquid and a xylooligosaccharide according to [6], wherein Step (1) is a step of hydrolyzing, with the filamentous fungus-derived cellulase, a product obtained by washing a solid component contained in the pretreated product of the cellulose-containing biomass with water.

[8] The method of producing a sugar liquid and a xylooligosaccharide according to any one of [1] to [7], wherein the xylan-containing material is a pretreated product of a cellulose-containing biomass.

[9] The method of producing a sugar liquid and a xylooligosaccharide according to [8], wherein the xylan-containing material is a solution component obtained by solid-liquid separation of the pretreated product of the cellulose-containing biomass.

[10] The method of producing a sugar liquid and a xylooligosaccharide according to [8], wherein the xylan-containing material is a solid component obtained by solid-liquid separation of the pretreated product of the cellulose-containing biomass.

[11] The method according to [10], which is a method of producing a sugar liquid and a xylooligosaccharide in which a process containing the Steps (1) to (3) is repeated, wherein a hydrolysis residue obtained in Step (3) is used as part or all of the cellulose-containing biomass in Step (1) in a later process(es).

By reusing recovered cellulase obtained in a process of production of a sugar liquid from cellulose-containing biomass in production of a xylooligosaccharide, the production cost of the sugar liquid and the xylooligosaccharide can be reduced.

BRIEF DESCRIPTION OF THE DRAWINGS

FIG. 1 is a schematic diagram showing an example of the method of producing a sugar liquid and a xylooligosaccharide.

DETAILED DESCRIPTION

Step (1): A Step of Hydrolyzing a Cellulose-Containing Biomass with a Filamentous Fungus-Derived Cellulase The cellulose-containing biomass means a biological resource containing a cellulose component. Cellulose is one of the major components of the plant cell wall, and is a polymer of glucose linked through β-1,4 bonds. The biological resource containing a cellulose component is not limited, and examples of the biological resource that may be used include Spermatophyta, Pteridophyta, Bryophyta, algae, and water plants, as well as waste building materials. Spermatophyta can be divided into gymnosperms and angiosperms. Both of these may be preferably used. Specific examples of the gymnosperms include Japanese cedar and pines. Angiosperms can be divided into monocotyledons and dicotyledons. Both of these may be preferably used. Specific examples of the monocotyledons include bagasse, switchgrass, napier grass, *Erianthus*, corn stover, corn cob, rice straw, wheat straw, bamboo, and bamboo grass. Specific examples of the dicotyledons include beet pulp, *Eucalyptus*, oak, *Betula alba*, poplar, and Japanese cypress.

In many cases, these kinds of cellulose-containing biomass also contain hemicellulose, which is a polysaccharide present between cellulose microfibrils. Thus, the hydrolysate of cellulose-containing biomass obtained in Step (1) contains not only glucose, which is a cellulose-derived sugar, but also xylose, arabinose, mannose and the like which are hemicellulose-derived sugars.

Further, since the cellulose-containing biomass also contains an aromatic macromolecule lignin, proteins and the like, the cellulose-containing biomass is preferably subjected to pretreatment before use to increase the efficiency of the hydrolysis using the filamentous fungus-derived cellulase. Examples of the method of the pretreatment include acid treatment using sulfuric acid, acetic acid or the like; alkali treatment using caustic soda, ammonia or the like; hydrothermal treatment; subcritical water treatment; pulverization treatment; steaming treatment; and chemical pulping treatment (for example, sulfite cooking and kraft cooking). When the cellulose-containing biomass is subjected to the pretreatment, part of hemicellulose may be hydrolyzed, and solubilization of xylose, arabinose, mannose and the like as well as polysaccharides and oligosaccharides constituted by these sugars may occur.

When a pretreated product of the cellulose-containing biomass is used in Step (1), either a state where both the solid component and the solution component are contained, or a state where the solution component, containing xylose and the like, has been removed by solid-liquid separation and/or washing of the solid component, may be employed.

The method of the pretreatment of the cellulose-containing biomass is not limited. Cellulase recovered from a hydrolysate of a chemical pulp product of cellulose-containing biomass is preferably used for the production of the xylooligosaccharide carried out later in Step (3). To reduce the overall cost of the process of simultaneously producing the sugar liquid and the xylooligosaccharide, the cellulose-containing biomass used in Step (1) and the xylan-containing material used in Step (3) are preferably pretreated products obtained from the same cellulose-containing biomass. As described later, a xylan-containing material obtained by hydrothermal treatment or alkali treatment of cellulose-containing biomass is preferably used in Step (3). Therefore, the cellulose-containing biomass used in Step (1) may also be such a pretreated product. Either a single pretreatment method or a combination of a plurality of pretreatment methods may be used to prepare the cellulose-containing biomass and the xylan-containing material. For example, when pretreatment hydrolysis such as hydrothermal treatment is carried out as a preceding process of chemical pulping, the xylan-containing material may be recovered as the solution component, and the solid component may then be subjected to chemical pulping to be used as the cellulose-containing biomass.

Since the recovered cellulase obtained in Step (2) is used for production of the xylooligosaccharide in Step (3), the β-xylosidase activity of the recovered cellulase is preferably lower than that of the filamentous fungus-derived cellulase used in Step (1) as described later. The smaller the amount of electrolytes contained in the hydrolysate in Step (1), the more easily the recovered cellulase having low β-xylosidase activity can be obtained. That is, the lower the electric conductivity of the hydrolysate in Step (1), the better. More specifically, the electric conductivity is preferably less than 16 mS/cm. The electric conductivity is more preferably less than 10 mS/cm. The electric conductivity is the reciprocal of the electric resistance of a solution. The method of measuring the electric conductivity is specified in JIS K 0130 "General rules for electrical conductivity measuring method". The electric conductivity of a solution is expressed as the reciprocal of the electric resistance measured in a container filled with the aqueous electrolyte solution in which two flat electrodes having an area of 1 m$^2$ face each other at a distance of 1 m. The more electrolytes contained in the solution, the higher the value of the electric conductivity. The electric conductivity is an index of the electrolyte concentration in the hydrolysate of the cellulose-containing biomass. Therefore, when a solid component is remaining in the hydrolysate, the electric conductivity means the electric conductivity of the solution component obtained by solid-liquid separation by, for example, centrifugation and/or filtration.

The method of adjusting the electric conductivity of the hydrolysate in Step (1) to less than 16 mS/cm may be, for example, a method in which the solid component obtained by pretreatment of the cellulose-containing biomass is washed with water to remove electrolytes, to adjust the electric conductivity of the hydrolysate to a desired value. By decreasing the electric conductivity of the hydrolysate, a recovered cellulase having lower β-xylosidase activity than the cellulase used in Step (1) can be obtained in Step (2), and the recovered cellulase can be preferably used in the xylooligosaccharide production process in Step (3).

The solid concentration of the cellulose-containing biomass in the hydrolysis reaction is not limited, and preferably 1 to 30% by weight. The lower the solid concentration, the lower the concentration of the sugar produced by the hydrolysis so that use of the hydrolysate as a fermentation feedstock may be difficult. On the other hand, when the concentration is too high, handling of the hydrolysate may be difficult. The weight of the cellulose-containing biomass herein is calculated using the absolute dry weight. The absolute dry weight means the weight after drying the cellulose-containing biomass at 105° C. until a constant weight is achieved. The measurement of the absolute dry weight can be carried out by drying the cellulose-containing biomass using a drier at 105° C. until the weight change of the biomass does not occur. The absolute dry weight of the xylan-containing biomass can be calculated by the same method.

Examples of the filamentous fungus from which the cellulase is to be derived include microorganisms such as *Trichoderma*, *Aspergillus*, *Cellulomonas*, *Clostridium*, *Streptomyces*, *Humicola*, *Acremonium*, *Irpex*, *Mucor*, and *Talaromyces*. The cellulase may also be a cellulase derived from a mutant strain prepared by subjecting such a microorganism to mutagenesis using a mutagen, UV irradiation, or the like to improve the cellulase productivity.

Among the filamentous fungi, *Trichoderma* fungi can be preferably used since they produce large amounts of enzyme components having high cellulose-hydrolyzing activities, into the culture liquid. Specific examples of the *Trichoderma*-derived cellulase include cellulases derived from *Trichoderma reesei* QM9414, *Trichoderma reesei* QM9123, *Trichoderma reesei* RutC-30, *Trichoderma reesei* PC3-7, *Trichoderma reesei* CL-8247, *Trichoderma reesei* MCG77, *Trichoderma reesei* MCG80, and *Trichoderma viride* QM9123. These cellulases may be used either individually or as a mixture. Among the *Trichoderma* microorganism-derived cellulases described above, cellulases derived from *Trichoderma reesei* are more preferred.

Filamentous fungus-derived cellulase is an enzyme composition having an activity to produce monosaccharides such as glucose and xylose by hydrolysis of cellulose and/or hemicellulose. The cellulase preferably contains, as an enzyme component(s), one or more selected from the group consisting of cellobiohydrolase, endoglucanase, β-glucosidase, xylanase, and β-xylosidase. Examples of enzyme components of cellulases derived from *Trichoderma reesei* include cellobiohydrolase I, cellobiohydrolase II, endoglucanase I, endoglucanase III, β-glucosidase, xylanase, and β-xylosidase. Since efficient hydrolysis of cellulose and/or hemicellulose can be carried out by a synergistic effect or a complementary effect of such a plurality of enzyme components, a cellulase derived from *Trichoderma reesei* is preferably used.

Cellobiohydrolase is a general term for enzymes that release cellobiose by hydrolysis of a cellulose chain. The group of enzymes belonging to cellobiohydrolase are described as EC number: EC 3.2.1.91. Cellobiohydrolase I begins the hydrolysis reaction in the reducing-end side of the cellulose chain, and cellobiohydrolase II begins the hydrolysis reaction in the non-reducing-end side of the cellulose chain.

Endoglucanase is a general term for enzymes that hydrolyze a cellulose chain from its central portion. The group of enzymes belonging to endoglucanase are described as EC number: EC 3.2.1.4.

β-Glucosidase is a general term for enzymes that act on cellooligosaccharides or cellobiose. The group of enzymes belonging to β-glucosidase are described as EC number: EC 3.2.1.21.

Xylanase is a general term for enzymes that act on hemicellulose or especially xylan. The group of enzymes belonging to xylanase are described as EC number: EC 3.2.1.8.

β-Xylosidase is a general term for enzymes that act on xylooligosaccharides. The group of enzymes belonging to xylosidase are described as EC number: EC 3.2.1.37.

Such cellulase components can be separated by a known method such as gel filtration, ion exchange, or two-dimensional electrophoresis, and the separated components can be subjected to determination of their amino acid sequences (by N-terminal analysis, C-terminal analysis, or mass spectrometry) and identification by comparison with databases.

The enzyme activity of a filamentous fungus-derived cellulase can be evaluated based on its hydrolytic activity on a substrate polysaccharide such as crystalline cellulose, carboxymethylcellulose (CMC), cellobiose, xylan, or mannan. Cellobiohydrolase, which hydrolyzes cellulose from its end portions, is a major enzyme that shows the crystalline cellulose-degrading activity. β-Glucosidase is a major enzyme that shows the cellobiose-degrading activity. Cellobiohydrolase and endoglucanase are major enzymes involved in the CMC-degrading activity. Xylanase and β-xylosidase are major enzymes that show the xylan-degrading activity. The term "major" herein is used to mean that the enzyme(s) is/are known to be involved in the degradation to the highest extent, and the term also means that other enzyme components are also involved in the degradation.

Alternatively, the activity of each enzyme may be measured by using a sugar derivative substrate such as a 4-nitrophenyl sugar derivative or a 4-methylumbelliferyl sugar derivative, and quantifying a dye released by hydrolysis reaction.

Since filamentous fungi produce cellulase into the culture liquid, the culture liquid may be used as it is as a crude enzyme agent, or a group of enzymes may be purified and formulated by a known method, and the resulting product may be used as a filamentous fungus-derived cellulase mixture. When the filamentous fungus-derived cellulase is purified and formulated, the resulting cellulase formulation may also contain substances other than enzymes such as protease inhibitors, dispersants, solubilizers, and stabilizers. Among these, a crude enzyme product is preferably used. The crude enzyme product is derived from a culture supernatant obtained by culturing a filamentous fungus for an arbitrary period in a medium prepared such that the microorganism produces cellulase. The medium components to be used therefor are not limited, and a medium supplemented with cellulose to promote production of cellulase may be generally used. As a crude enzyme product, the culture liquid may be used as it is, or the culture supernatant processed only by removal of the filamentous fungus may be preferably used.

The weight ratios of enzyme components in the crude enzyme product are not limited. For example, a culture liquid derived from *Trichoderma reesei* contains 50 to 95% by weight of cellobiohydrolase, and also contains as other components endoglucanase, β-glucosidase and the like.

Microorganisms belonging to *Trichoderma* produce strong cellulase components into the culture liquid, while the β-glucosidase activity in the culture liquid is low since β-glucosidase is mostly retained in the cells or on the cell surfaces. Therefore, β-glucosidase from a different species or from the same species may be added to the crude enzyme product. As the β-glucosidase from a different species, β-glucosidase derived from an *Aspergillus* microorganism may be preferably used. Examples of the β-glucosidase derived from an *Aspergillus* microorganism include Novozyme 188, which is commercially available from Novozyme. Alternatively, a gene may be introduced into a *Trichoderma* microorganism to prepare a *Trichoderma* microorganism that has undergone genetic recombination such that β-glucosidase is produced into the culture liquid, and the microorganism may be cultured to provide a culture liquid having improved β-glucosidase activity.

The temperature during the hydrolysis reaction is not limited as long as it satisfies the preferred reaction conditions for filamentous fungus-derived cellulase. The temperature is preferably 30 to 75° C. and, especially when a *Trichoderma*-derived cellulase is used, the temperature is more preferably 40 to 60° C.

The pH during the hydrolysis reaction is also not limited as long as it satisfies the preferred reaction conditions for filamentous fungus-derived cellulase. The pH is preferably 3.0 to 7.0, more preferably 4.0 to 6.0. When a *Trichoderma* microorganism-derived cellulase is used as the filamentous fungus-derived cellulase, the optimum reaction pH is 5.0. Since the pH changes during the hydrolysis, it is preferred to perform the hydrolysis while maintaining a constant pH by addition of a buffer to the reaction liquid or use of an acid or an alkali.

The time of the hydrolysis reaction is preferably 2 hours to 200 hours. When the reaction time is less than 2 hours, the sugar yield may be insufficient. On the other hand, when the time of the hydrolysis reaction exceeds 200 hours, deactivation of the cellulase may proceed and, therefore, reuse of the recovered cellulase may be adversely affected.

Step (2): A Step of Subjecting the Hydrolysate of Step (1) to Solid-Liquid Separation, and Filtering the Solution Component Through an Ultrafiltration Membrane to Recover a Recovered Cellulase as a Non-Permeate, and to Recover a Sugar Liquid as a Permeate The solution component obtained by solid-liquid separation of the hydrolysate obtained in Step (1) contains a filamentous fungus-derived cellulase component and a sugar component. These components can be separated from each other by filtration using an ultrafiltration membrane.

The method of the solid-liquid separation is not limited, and specific examples of the method include centrifugation and press filtration.

The ultrafiltration membrane means a membrane having a molecular weight cutoff of 300 to 200,000, and is referred to as UF membrane or the like for short. Since the pore size of an ultrafiltration membrane is too small, measurement of the pore size on its membrane surface is difficult even under the electron microscope or the like. Therefore, a value called the molecular weight cutoff is used as an index of the pore size instead of the average pore size. According to the Membrane Society of Japan ed., Membrane Experiment Series, Vol. III, Artificial Membrane, editorial committee members: Shoji Kimura, Shin-ichi Nakao, Haruhiko Ohya, and Tsutomu Nakagawa (1993, Kyoritsu Shuppan Co., Ltd.), p. 92, "The curve obtained by plotting the molecular weight of the solute along the abscissa and the blocking rate along the ordinate is called the molecular weight cutoff curve. The molecular weight with which the blocking rate reaches 90% is called the molecular weight cutoff of the membrane." Thus, the molecular weight cutoff is well-known to those skilled in the art as an index of the membrane performance of an ultrafiltration membrane.

In the separation of the filamentous fungus-derived cellulase and the sugar component from each other using the ultrafiltration membrane, the molecular weight cutoff is not limited as long as its allows permeation of glucose (molecular weight, 180) and xylose (molecular weight, 150), which are major monosaccharide components of the sugar liquid, while it blocks filamentous fungus-derived cellulase. The molecular weight cutoff is preferably 500 to 100,000. From the viewpoint of securing the yield of the filamentous fungus-derived cellulase component while separating impurities that show inhibitory actions against the enzymatic reaction from the filamentous fungus-derived cellulase, the molecular weight cutoff is more preferably 5000 to 50,000. The molecular weight cutoff is still more preferably 10,000 to 30,000.

Examples of the material of the ultrafiltration membrane include polyether sulfone (PES), polysulfone (PS), polyacrylonitrile (PAN), polyvinylidene fluoride (PVDF), regenerated cellulose, cellulose, cellulose ester, sulfonated polysulfone, sulfonated polyether sulfone, polyolefin, polyvinyl alcohol, polymethyl methacrylate, and polytetrafluoroethylene. Since regenerated cellulose, cellulose, and cellulose ester undergo degradation by filamentous fungus-derived cellulase, an ultrafiltration membrane using a synthetic polymer material such as PES or PVDF is preferably used.

Examples of the method of filtration through an ultrafiltration membrane include dead-end filtration and cross-flow filtration, and the method is preferably cross-flow filtration in view of suppression of membrane fouling. Examples of the form of the ultrafiltration membrane which may be used as appropriate include the flat membrane, spiral-wound membrane, tubular membrane, and hollow fiber membrane. Specific examples of the ultrafiltration membrane include Type G-5, Type G-10, Type G-20, Type G-50, Type PW, and Type HWSUF, manufactured by DESAL; HFM-180, HFM-183, HFM-251, HFM-300, HFK-131, HFK-328, MPT-U20, MPS-U20P, and MPS-U20S, manufactured by KOCH; SPE1, SPE3, SPE5, SPE10, SPE30, SPV5, SPV50, and SOW30, manufactured by Synder; products of MICROZA® UF series, manufactured by Asahi Kasei Corporation, having molecular weight cutoffs of 3000 to 10,000; and NTR7410 and NTR7450, manufactured by Nitto Denko Corporation.

Part of the enzyme components of the filamentous fungus-derived cellulase used in Step (1) are adsorbed to solid components such as undegraded cellulose and lignin in the hydrolysis reaction of the cellulose-containing biomass. The cellulase components are not evenly adsorbed, and the recovered cellulase obtained as the non-permeate in the filtration through the ultrafiltration membrane has a reduced β-xylosidase activity compared to the filamentous fungus cellulase used in Step (1). It can therefore be preferably used for the production of a xylooligosaccharide in the later-mentioned Step (3). The lower the β-xylosidase activity in the recovered cellulase, the better. The β-xylosidase activity in the recovered cellulase is preferably reduced to less than 5% relative to that in the filamentous fungus-derived cellulase used in Step (1).

More specifically, as a result of the reduction of the β-xylosidase activity in the recovered cellulase, the β-xylosidase activity in the recovered cellulase is preferably reduced to less than 0.01 U/mg protein in the recovered cellulase. The β-xylosidase activity can be measured by using 4-nitrophenyl-β-D-xylopyranoside as a substrate, and quantifying 4-nitrophenol released by hydrolysis reaction by colorimetry.

For production of a xylooligosaccharide in Step (3) using the recovered cellulase, the recovered cellulase preferably contains at least xylanase. Xylanase catalyzes a reaction in which a xylan backbone is hydrolyzed in its middle portion to produce a xylooligosaccharide. In filamentous fungus-derived cellulase, genes encoding xylanase such as xyn1 (GH11), xyn2 (GH11), xyn3 (GH10), xyn4 (GH5), xyn5b (GH5), and xyn11 (GH11) are known.

Since the sugar liquid collected as the permeate in the filtration through the ultrafiltration membrane contains as major components glucose and xylose, which are monosaccharides, the sugar liquid can be used as it is as a fermentation feedstock in the later-described fermentation step. However, concentration treatment may further be carried out for increasing the sugar concentration to increase the efficiency of the fermentation step. Examples of the concentration treatment for the sugar liquid include concentration by evaporation, concentration under reduced pressure, and membrane concentration. The method described in WO 2010/067785, in which filtration through a nanofiltration membrane and/or reverse osmosis membrane is carried out, and which uses less energy and enables separation of fermentation inhibitors contained in the sugar liquid, can be employed for obtaining a concentrated sugar liquid in which sugar components are concentrated.

Production of various chemical products is possible by culturing microorganisms having capacities to produce them using the sugar liquid obtained by our methods as a fermentation feedstock. Growing a microorganism using a fermentation feedstock herein means that sugar components and/or amino sources contained in the sugar liquid are used as nutrients for allowing the growth and maintenance of the microorganism. Such chemical products are produced and accumulated inside and outside the living body in the process of metabolism using sugar components in the sugar liquid as carbon sources. Specific examples of the chemical products include alcohols such as ethanol, 1,3-propanediol, 1,4-propanediol, and glycerol; organic acids such as acetic acid, lactic acid, pyruvic acid, succinic acid, malic acid, itaconic acid, and citric acid; nucleosides such as inosine and guanosine; nucleotides such as inosinic acid and guanylic acid; and amine compounds such as cadaverine. Further, the sugar liquid can be applied to production of enzymes, antibiotics, recombinant proteins and the like.

Step (3): A Step of Reacting the Recovered Cellulase in Step (2) with a Xylan-Containing Material, and Recovering a Xylooligosaccharide Produced As described above, the recovered cellulase in Step (2) has a reduced β-xylosidase activity compared to the filamentous fungus-derived cellulase used in Step (1). It can therefore be preferably used for production of a xylooligosaccharide from a xylan-containing material.

The xylan-containing material is not limited as long as it contains xylan. Xylan is a constituting component of hemicellulose present in the cell wall of plant cells. It is a heterosaccharide in which various side chains are bound to the xylose backbone linked through β-1,4 bonds. Xylan has a variety of structures, and its structure is different among plant species. For example, as a xylan contained in monocotyledons, arabinoxylan is known. It has arabinose residues in its side chains. On the other hand, as xylans contained in dicotyledons, glucuronoarabinoxylan and glucuronoxylan are known. They have glucuronic acid residues and arabinose residues in their side chains. Further, as a xylan contained in dicotyledons, especially in hardwoods, 4-O-methylglucuronoxylan is known. It has 4-O-methylglucuronic acid residues in its side chains. Further, as a xylan contained in gymnosperms, 4-O-methylglucuronoarabinoxylan is known. It has arabinose residues and 4-O-methylglucuronic acid residues in its side chains. The xylan-containing material may contain any of these.

Thus, the biomass derived from a biological resource mentioned as the cellulose-containing biomass in Step (1) may also be used as the xylan-containing material. Specific examples of the monocotyledons include bagasse, switchgrass, napier grass, *Erianthus*, corn stover, corn cob, rice straw, wheat straw, bamboo, and bamboo grass. Specific examples of the dicotyledons include hardwoods such as *Eucalyptus*, oak, and *Betula alba*, as well as waste wood thereof.

As mentioned in Step (1), pretreatment improves the hydrolysis efficiency of the enzyme. Thus, when these kinds of cellulose-containing biomass are used as the xylan-containing material in Step (3), pretreatment is preferably carried out similarly to Step (1). Examples of the method of the pretreatment include, similarly to the pretreatment in Step (1), acid treatment using sulfuric acid, acetic acid or the like; alkali treatment using caustic soda, ammonia, or the like; hydrothermal treatment; subcritical water treatment; pulverization treatment; steaming treatment; and chemical pulping treatment (more specifically, for example, sulfite cooking and kraft cooking). To obtain a high xylooligosaccharide yield, the method of the pretreatment is preferably a method which can suppress degradation of xylan to xylose as much as possible. More specifically, the method of the pretreatment is preferably hydrothermal treatment or alkali treatment.

When the xylan-containing material is a pretreated product of a cellulose-containing biomass, xylan is present as a solid component in some cases, while xylan is dissolved as a solution component in other cases, depending on the pretreatment method. In both cases, the pretreated product containing xylan may be used as the xylan-containing material. The pretreated product may be used as the xylan-containing material in a state where both the solution component and the solid component are contained, or solid-liquid separation may be carried out to use only the fraction containing xylan. From the viewpoint of producing a xylooligosaccharide having high purity, it is preferred to perform solid-liquid separation to use only the fraction containing xylan as the xylan-containing material.

As mentioned in Step (1), either a single pretreatment method or a combination of a plurality of pretreatment methods such as hydrothermal treatment and chemical pulping treatment may be used to prepare the cellulose-containing biomass and the xylan-containing material. Since the xylan-containing solution component obtained by the pretreatment of the cellulose-containing biomass contains impurities such as lignin in many cases, a product prepared by removal of such impurities by a method such as membrane separation or solvent extraction may be used as the xylan-containing material.

When xylan is dissolved as a solution component by the pretreatment of the cellulose-containing biomass, it is preferred to perform solid-liquid separation of the pretreated product of the cellulose-containing biomass, and to subject only the solution component to the hydrolysis in Step (3) as the xylan-containing material. In such cases, by hydrolyzing the solid component as the cellulose-containing biomass in Step (1), the cellulose-containing biomass and the xylan-containing material can be obtained at the same time by one time of pretreatment, which is advantageous from the viewpoint of reducing the production cost.

When the xylan contained in the pretreated cellulose-containing biomass is a solid component, the solid component may be hydrolyzed in Step (3) as the xylan-containing material, and the resulting xylooligosaccharide may be recovered. By using the hydrolysis residue of Step (3) as the cellulose-containing biomass in Step (1) of the next cycle, a sugar liquid can be produced from cellulose remaining in the hydrolysis residue. That is, since the hydrolysis residue of the xylan-containing material can be reused as the cellulose-containing biomass, the production cost can be advantageously reduced.

When the xylan-containing material is a solid component, the solid concentration in the hydrolysis reaction is not limited, and is preferably 1 to 30% by weight. When the solid concentration is low, the amount of liquid required for obtaining a sufficient yield of xylooligosaccharide increases, which may be disadvantageous in the later xylooligosaccharide purification step. On the other hand, when the solid concentration is too high, handling of the hydrolysate may be difficult.

Similarly to Step (1), the temperature during the hydrolysis reaction is not limited as long as it satisfies the preferred reaction conditions for filamentous fungus-derived cellulase. The temperature is preferably 30 to 75° C., and, especially when a *Trichoderma* microorganism-derived cellulase is used in Step (1), the temperature is more preferably 40 to 60° C.

The pH during the hydrolysis reaction is also not limited as long as it satisfies the preferred reaction conditions for filamentous fungus-derived cellulase. The pH is preferably 3.0 to 7.0, more preferably 4.0 to 6.0. When a *Trichoderma* microorganism-derived cellulase is used in Step (1), the optimum reaction pH is 5.0. Since the pH changes during the hydrolysis, it is preferred to perform the hydrolysis while maintaining a constant pH by addition of a buffer to the reaction liquid or use of an acid or alkali.

The time of the hydrolysis reaction is preferably 10 minutes to 48 hours. The xylooligosaccharide preferably has a degree of polymerization of 2 to 10. In particular, the xylooligosaccharide preferably contains as a major component(s) a xylooligosaccharide(s) having a degree(s) of polymerization of 2 (xylobiose) and/or a degree of polymerization of 3 (xylotriose), which is/are highly assimilable by lactic acid bacteria and bifidobacteria, which are intestinal bacteria. When the reaction time is less than 10 minutes, a sufficient yield of xylooligosaccharide cannot be obtained in some cases. On the other hand, when the reaction time is too long, degradation of xylooligosaccharide may occur due to the action(s) of β-xylosidase and/or xylanase remaining in a small amount(s) in the recovered cellulase, leading to an increase in xylose, which is a monosaccharide. The reaction is therefore preferably completed within 48 hours.

The xylooligosaccharide liquid produced by the action of the recovered cellulase also contains other kinds of impurities and residual matters. Therefore, purification of xylooligosaccharide may be carried out by filtration, or by using an absorbent such as an ion-exchange resin, synthetic adsorbent, or active carbon. When an absorbent is used, coloring components derived from the xylan-containing material can be removed so that applicability of the xylooligosaccharide to processed foods, processing of beverages, and the like can be increased. The obtained xylooligosaccharide liquid may be pulverized when necessary.

EXAMPLES

Our methods are described below more concretely by way of Examples. However, this disclosure is not limited to these examples.

Reference Example 1 Preparation of *Trichoderma* Microorganism-Derived Cellulase

*Trichoderma* microorganism-derived cellulase was prepared by the following method.
Preculture A solution of 5% (w/v) corn steep liquor, 2% (w/v) glucose, 0.37% (w/v) ammonium tartrate, 0.14% (w/v) ammonium sulfate, 0.14% (w/v) potassium dihydrogen phosphate, 0.03% (w/v) calcium chloride dihydrate, 0.03% (w/v) magnesium sulfate heptahydrate, 0.02% (w/v) zinc chloride, 0.01% (w/v) iron (III) chloride hexahydrate, 0.004% (w/v) copper (II) sulfate pentahydrate, 0.0008% (w/v) manganese chloride tetrahydrate, 0.0006% (w/v) boric acid, and 0.026% (w/v) hexaammonium heptamolybdate tetrahydrate in RO water was prepared, and 100 mL of this solution placed in a baffled 500-mL Erlenmeyer flask, followed by sterilization by autoclaving at 121° C. for 15 minutes. After allowing the solution to cool, PE-M and Tween 80 separately sterilized by autoclaving at 121° C. for 15 minutes were added to the solution to a concentration of 0.01% (w/v) each. To the resulting preculture medium, *Trichoderma reesei* QM9414 was inoculated at $1 \times 10^5$ cells/mL, and the cells were cultured at 28° C. for 72 hours with shaking at 180 rpm, to provide a preculture liquid (shaker: BIO-SHAKER BR-40LF, manufactured by TAITEC CORPORATION).
Main Culture A solution of 5% (w/v) corn steep liquor, 2% (w/v) glucose, 10% (w/v) cellulose (Avicel), 0.37% ammonium tartrate (w/v), 0.14% (w/v) ammonium sulfate, 0.2% (w/v) potassium dihydrogen phosphate, 0.03% (w/v) calcium chloride dihydrate, 0.03% (w/v) magnesium sulfate heptahydrate, 0.02% (w/v) zinc chloride, 0.01% (w/v) iron (III) chloride hexahydrate, 0.004% (w/v) copper (II) sulfate pentahydrate, 0.0008% (w/v) manganese chloride tetrahydrate, 0.006% (w/v) boric acid, and 0.0026% (w/v) hexaammonium heptamolybdate tetrahydrate in distilled water was prepared, and 2.5 L of this solution placed in a 5-L jar fermenter (manufactured by ABLE, DPC-2A), followed by sterilization by autoclaving at 121° C. for 15 minutes. After allowing the solution to cool, PE-M and Tween 80 separately sterilized by autoclaving at 121° C. for 15 minutes were added to the solution to a concentration of 0.01% (w/v) each. To the resulting mixture, 250 mL of the preculture liquid obtained by the above method was inoculated. The cells were then cultured at 28° C. for 87 hours at 300 rpm at an aeration rate of 1 vvm. The obtained culture liquid was centrifuged, and the culture supernatant used as a crude enzyme liquid. As a result of measurement of the protein concentration in the culture supernatant according to the later-described Reference Example 2, the protein concentration was 10 g/L.

Reference Example 2 Measurement of Protein Concentration

For the protein concentration, a commercially available reagent for measurement of the protein concentration (Quick Start Bradford Protein Assay, manufactured by Bio-Rad) was used. To 250 μL of the reagent for measurement of the protein concentration that had been brought to room temperature, 5 µL of a diluted cellulase solution was added, and the resulting mixture was left to stand at room temperature for 5 minutes. The absorbance at 595 nm was then measured using a microplate reader (Multiskan GO, manufactured by Thermo Scientific). Using an aqueous bovine serum albumin solution as a standard solution, the protein concentration in the cellulase solution was calculated by referring to a calibration curve.

Reference Example 3 Measurement of Sugar Concentrations

The concentrations of glucose, xylose, xylobiose, and xylotriose contained in the sugar liquid were measured under the HPLC conditions described below based on comparison with standard samples.
Column: AQUITY UPLC BEH Amide (manufactured by Waters)
Mobile phase A: 80% acetonitrile+0.1% TFA
Mobile phase B: 30% acetonitrile+0.1% TFA
Flow rate: 0.12 mL/min.
The ratio of the mobile phase B was gradually increased from 0% such that it reaches 40% at Minute 10. At Minute 10.01, only mobile phase A was used again, and the analysis was continued until Minute 20.
Detection method: ELSD (evaporative light scattering detector)
Temperature: 55° C.

Reference Example 4 Method of Measuring β-Xylosidase Activity

As the β-xylosidase activity, the degradation activity for 4-nitrophenyl-β-D-xylopyranoside (pNP-Xyl) was measured. To 0.9 mL of 55 mM acetate buffer (pH 5.0) containing 1.1 mM of a substrate, 0.1 mL of an enzyme liquid was added, and the reaction was allowed to proceed accurately at 30° C. for 30 minutes (final concentration of the substrate, 1 mM; final concentration of the buffer, 50 mM). Thereafter, 0.1 mL of 2 M aqueous sodium carbonate solution was added to the reaction solution to stop the reaction, followed by measurement of the absorbance at 405 nm (OD test). To provide a blank, a mixture prepared by adding 2 M aqueous sodium carbonate solution and the enzyme liquid to the substrate solution in this order was similarly subjected to measurement of the absorbance at 405 nm (OD blank). The amount of enzyme that produces 1 µmol of 4-nitrophenol per minute in the above reaction system was defined as 1 U, and the activity value (U/mL) was calculated according to the following equation. The millimolar absorption coefficient of 4-nitrophenol in the above reaction system is 17.2 L/mmol/cm.

3-Xylosidase activity (U/mL)={(OD test−OD blank)×1.1 (mL)×enzyme dilution rate}/{17.2× 30 (minutes)×0.1 (mL)}

Reference Example 5 Pretreatment of Cellulose-Containing Biomass

As the cellulose-containing biomass, three kinds of pretreated products (oak, bagasse, and *Betula alba*) were used. As the oak, a pulped product (Hyogo Pulp Co., Ltd.) was used to provide oak pretreated product 1. The bagasse and *Betula alba* were pretreated by the following procedure, and provided as bagasse pretreated products 1 to 4 and *Betula alba* pretreated products 1 to 3, respectively.

(1) Hydrothermal Treatment of Bagasse
Bagasse was slurried (solid concentration, 30% by weight), and treated at 200° C. for 10 minutes. After the hydrothermal treatment, solid-liquid separation was carried out. The solid component was sufficiently washed to provide the bagasse pretreated product 1, and the solution was provided as the bagasse pretreated product 2.
(2) Alkali Treatment of Bagasse
A slurry having a solid concentration of 30% by weight supplemented with 100 mg of sodium hydroxide per 1 g of the solid component of bagasse was treated at 180° C. for 10 minutes. After the alkali treatment, solid-liquid separation was carried out. The solid component was sufficiently washed to provide the bagasse pretreated product 3, and the solution was provided as the bagasse pretreated product 4.
(3) Hydrothermal Treatment of *Betula alba*
A slurry of *Betula alba* chips (solid concentration, 30% by weight) was treated at 150° C. for 4 hours. After the hydrothermal treatment, solid-liquid separation was carried out. The solid component was sufficiently washed to provide the *Betula alba* pretreated product 1, and the solution was provided as the *Betula alba* pretreated product 2.
(4) Acetone Fraction of *Betula alba* Pretreated Product 2
Cold acetone in the same amount as the *Betula alba* pretreated product 2 obtained in the previous Section (3) was added, and the resulting mixture was stirred for 5 minutes on ice, followed by leaving the mixture to stand at room temperature. One hour later, filtration was carried out, and the obtained solid component was dried to provide the *Betula alba* pretreated product 3.

Reference Example 6 Hydrolysis of Cellulose-containing Biomass with *Trichoderma* Microorganism-derived Cellulase and Preparation of Recovered Cellulase Step 1: Hydrolysis of Cellulose-Containing Biomass
As the cellulose-containing biomass, the oak pretreated product, the bagasse pretreated product 1, or the bagasse pretreated product 3 was used. In a 50-mL centrifuge tube, 1 g (absolute dry weight) of each pretreated product was taken, and RO water was added thereto to provide a slurry. The moisture content was measured using an infrared moisture meter (manufactured by Kett Electric Laboratory, FD-720) by drying the sample at 105° C. The pH of the slurry was adjusted to a pH of 4.7 to 5.3 by addition of dilute sulfuric acid, and 1.0 mL of *Trichoderma* microorganism-derived cellulase prepared according to Reference Example 1 (protein concentration, 10 g/L) and 0.45 mL of *Aspergillus niger*-derived β-glucosidase (manufactured by Megazyme; E-BGLUC; protein concentration, 1.1 g/L) were added thereto. Finally, RO water was added thereto to a total weight of 10 g to adjust the final solid content to 10% by weight, and the resulting mixture was mixed by rotation using a hybridization rotator (manufactured by Nissin Rika, SN-06BN) at 50° C. for 24 hours.
Step 2: Preparation of Recovered Cellulase
The obtained hydrolysate was centrifuged (8000 G, 10 minutes) to perform solid-liquid separation, to obtain a solution component and a hydrolysis residue. The solution component collected was passed through a microfiltration membrane having a pore size of 0.2 µm (25 mm GD/X syringe filter; material, PVDF; manufactured by GE Healthcare Japan) to remove particulates, and then filtration was carried out using an ultrafiltration membrane having a molecular weight cutoff of 10,000 (VIVASPIN Turbo15; material, PES; manufactured by Sartorius stedim biotech).

The non-permeate side was collected as a recovered cellulase liquid, and the permeate side collected as a sugar liquid. The sugar liquid was subjected to measurement of sugar concentrations according to Reference Example 3. The recovered cellulase liquid was subjected to measurement of the β-xylosidase activity according to Reference Example 4. The sugar concentrations in each sugar liquid are shown in Table 1, and the β-xylosidase activity of each recovered cellulase liquid is shown in Table 2.

TABLE 1

| | Sugar concentration (g/L) | |
|---|---|---|
| | Glucose | Xylose |
| Oak pretreated product | 55 | 12 |
| Bagasse pretreated product 1 | 44 | 3.2 |
| Bagasse pretreated product 3 | 29 | 20 | the bagasse pretreated product 3 or the *Betula alba* pretreated product 3 was taken in a 50-mL centrifuge tube, and 1.0 mL of RO water or 1.0 mL of a *Trichoderma* microorganism-derived cellulase prepared according to Reference Example 1 was added thereto. The resulting mixture was mixed by rotation at 50° C. for 6 hours, and then centrifuged (8000 G, 10 minutes), followed by analyzing sugar concentrations in the supernatant according to Reference Example 3.

Example 1 Hydrolysis of Xylan-Containing Material Using *Trichoderma* Microorganism-Derived Cellulase Hydrolysis was carried out in the same manner as in Comparative Example 1 except that the whole recovered cellulase obtained according to Reference Example 6 was used instead of the *Trichoderma* microorganism-derived cellulase. The sugar concentrations observed in Compara-

TABLE 2

| | | Liquid volume (mL) | Protein concentration (g/L) | β-Xylosidase activity (U/mL) | | β-Xylosidase activity (B/A) × 100 (%) | β-Xylosidase activity per mg protein (U/mg) |
|---|---|---|---|---|---|---|---|
| | | | | | (U) | | |
| A. | *Trichoderma* microorganism-derived cellulase | 1.0 | 10 | 2.1 | 2.1 | (100) | (0.21) |
| B. Recovered cellulase | Recovered cellulase (oak pretreated product) | 1.8 | 5.2 | 0.019 | 0.034 | 1.6 | 0.0034 |
| | Recovered cellulase (bagasse pretreated product 1) | 1.4 | 4.3 | 0.014 | 0.019 | 0.9 | 0.0019 |
| | Recovered cellulase (bagasse pretreated product 3) | 1.7 | 3.3 | 0.011 | 0.019 | 0.9 | 0.0019 |

Comparative Example 1 Hydrolysis of Xylan-Containing Material Using Filamentous Fungus-Derived Cellulase As a xylan-containing material, 10 mL of the bagasse pretreated product 2, 10 mL of the *Betula alba* pretreated product 2, or 10 g of a slurry (solid concentration, 10% by weight; pH was adjusted to 5 using dilute sulfuric acid) of tive Example 1 and Example 1 are shown in Table 3. In both of the cases where a xylan-containing material derived from bagasse, which is a plant belonging to Poaceae, or *Betula alba*, which is a hardwood, was used, larger amounts of xylooligosaccharide could be produced by the reaction with the recovered cellulase as compared to when the reaction with the *Trichoderma* microorganism-derived cellulase was carried out.

TABLE 3

| | | | | Xylooligosaccharide (g/L) | | | | |
|---|---|---|---|---|---|---|---|---|
| | | Enzyme | Xylose (g/L) | Disaccharide | Tri-saccharide | Tetra-saccharide | Pentasaccharide | Total |
| Bagasse pretreated product 2 | Comparative Example 1 | Not added | 11.6 | 2.2 | 1.4 | 1.8 | 0.2 | 5.6 |
| | | *Trichoderma* microorganism-derived cellulase | 26.9 | Undetectable | Undetectable | Undetectable | Undetectable | — |
| | Example 1 | Recovered cellulase (oak pretreated product) | 14.0 | 12.6 | 3.3 | 0.77 | 0.21 | 16.9 |
| | | Recovered cellulase (bagasse pretreated product 1) | 13.2 | 12.9 | 3.5 | 0.78 | 0.20 | 17.4 |
| | | Recovered cellulase (bagasse pretreated product 3) | 12.1 | 12.5 | 3.4 | 0.86 | 0.33 | 17.1 |
| *Betula alba* pretreated product 2 | Comparative Example 1 | Not added | 17.3 | 3.1 | 1.8 | 1.2 | 0.5 | 6.6 |
| | | *Trichoderma* microorganism-derived cellulase | 28.2 | 2.3 | Undetectable | Undetectable | Undetectable | 2.3 |
| | Example 1 | Recovered cellulase (oak pretreated product) | 21.1 | 4.5 | 1.9 | 1.1 | 0.8 | 8.3 |
| | | Recovered cellulase (bagasse pretreated product 1) | 20.5 | 4.7 | 2.1 | 1.5 | 1.1 | 9.4 |
| | | Recovered cellulase (bagasse pretreated product 3) | 20.8 | 3.9 | 2.4 | 1.5 | 1.5 | 9.3 |
| Bagasse pretreated product 3 | Comparative Example 1 | Not added | 0.2 | 1.2 | 1.3 | 1.8 | 1.7 | 6.0 |
| | | *Trichoderma* microorganism-derived cellulase | 14.8 | 3.2 | Undetectable | Undetectable | Undetectable | 3.2 |

TABLE 3-continued

|  |  | Enzyme | Xylose (g/L) | Xylooligosaccharide (g/L) | | | | |
|---|---|---|---|---|---|---|---|---|
|  |  |  |  | Disaccharide | Tri-saccharide | Tetra-saccharide | Pentasaccharide | Total |
|  | Example 1 | Recovered cellulase (oak pretreated product) | 3.1 | 4.5 | 1.2 | 0.8 | 0.5 | 7.0 |
|  |  | Recovered cellulase (bagasse pretreated product 1) | 2.6 | 4.1 | 2.3 | 1.7 | 1.9 | 10.0 |
|  |  | Recovered cellulase (bagasse pretreated product 3) | 1.0 | 3.3 | 1.7 | 1.9 | 1.9 | 9.8 |
| Betula alba pretreated product 3 | Comparative Example 1 | Not added | Undetectable | Undetectable | Undetectable | Undetectable | Undetectable | — |
|  |  | Trichoderma microorganism-derived cellulase | 38.6 | 9.2 | 2.2 | 0.6 | 0.2 | 12.2 |
|  | Example 1 | Recovered cellulase (oak pretreated product) | 2.4 | 5.0 | 4.7 | 4.3 | 2.4 | 16.4 |
|  |  | Recovered cellulase (bagasse pretreated product 1) | 1.9 | 5.3 | 5.0 | 4.6 | 2.7 | 17.6 |
|  |  | Recovered cellulase (bagasse pretreated product 3) | 2.0 | 5.2 | 4.8 | 4.7 | 2.5 | 17.2 |

Example 2 Relationship Between Electric Conductivity of Cellulose-Containing Biomass and β-Xylosidase Activity of Recovered Cellulase A pretreated product of oak was hydrolyzed as a cellulose-containing biomass, and a recovered cellulase was prepared by the same method as in Reference Example 6. However, sodium chloride was added in the hydrolysis reaction to obtain hydrolysates having different electric conductivities.

Since the *Aspergillus niger*-derived β-glucosidase (manufactured by Megazyme; E-BGLUC; protein concentration, 1.1 g/L), which was used in Reference Example 6, is a product in which the enzyme is suspended in 3.2 M ammonium sulfate, it was desalted by water-adding filtration through an ultrafiltration membrane having a molecular weight cutoff of 10,000 (VIVASPIN Turbo15; material, PES; manufactured by Sartorius stedim biotech), to prepare a desalted enzyme solution as a result of 1000- or higher fold dilution. To the hydrolysates, sodium chloride was added such that each concentration shown in Table 4 was achieved, to prepare hydrolysates having the respective electric conductivities. The hydrolysates having electric conductivities of not less than 9.4 mS/cm were prepared using a non-desalted enzyme solution.

From each hydrolysate, a recovered cellulase liquid was obtained, and subjected to measurement of the β-xylosidase activity according to Reference Example 4. The electric conductivity of each hydrolysate and the β-xylosidase activity of each recovered cellulase are shown in Table 4. When the electric conductivity of the hydrolysate was less than 16.3 mS/cm, the β-xylosidase activity was less than 5%.

TABLE 4

| Electric conductivity of hydrolysate (mS/cm) | Sodium chloride concentration of hydrolysate (g/L) | Protein concentration (g/L) | Liquid volume (mL) | β-Xylosidase activity (U/mL) | β-Xylosidase activity (U) | β-Xylosidase activity (B/A) × 100 (%) | β-Xylosidase activity per mg protein (U/mg) |
|---|---|---|---|---|---|---|---|
| A. *Trichoderma* microorganism-derived cellulase — | — | 10 | 1.0 | 2.1 | 2.1 | (100) | (0.21) |
| B. Recovered cellulase  1.0 | — | 4.8 | 1.8 | 0.0035 | 0.0063 | 0.3 | 0.000063 |
| 5.4 | 3.0 | 4.6 | 1.9 | 0.0053 | 0.011 | 0.5 | 0.0011 |
| 9.4 (Reference Example 6) | — | 5.2 | 1.8 | 0.019 | 0.034 | 1.6 | 0.0034 |
| 13.1 | 3.0 | 5.1 | 1.9 | 0.031 | 0.059 | 2.8 | 0.0059 |
| 16.3 | 6.0 | 5.5 | 1.8 | 0.058 | 0.10 | 4.8 | 0.010 |
| 24.2 | 10 | 5.0 | 2.0 | 0.076 | 0.15 | 7.2 | 0.015 |
| 30.0 | 15 | 5.4 | 1.9 | 0.10 | 0.20 | 9.3 | 0.020 |

Example 3 Relationship Between β-Xylosidase Activity of Recovered Cellulase and Xylooligosaccharide Produced Using the recovered cellulase obtained in Example 2, hydrolysis of the bagasse pretreated product 2 was carried out by the same method as in Example 1. The concentrations of sugars in the supernatant are shown in Table 5.

From these results, we found that when a recovered cellulase is not used, xylan is degraded into a monosaccharide xylose, and xylooligosaccharide is not detected. In contrast, we found that, by using a recovered cellulase, a xylooligosaccharide can be obtained with high sugar yield. We also found that a xylooligosaccharide can be obtained with especially high sugar yield when the β-xylosidase activity after the recovery is as low as less than 5% relative to that before the recovery.

TABLE 5

| Electric conductivity of hydrolysate (mS/cm) | β-Xylosidase activity (B/A) × 100 (%) | Xylose (g/L) | Xylooligosaccharide (g/L) | | | | |
|---|---|---|---|---|---|---|---|
| | | | Disaccharide | Tri-saccharide | Tetrasaccharide | Penta-saccharide | Total |
| A. *Trichoderma* microorganism-derived cellulase | (100) (Comparative Example 1) | 26.9 | Undetectable | Undetectable | Undetectable | Undetectable | — |
| B. Recovered cellulase    1.0 | 0.3 (Example 4) | 12.1 | 12.4 | 3.9 | 0.88 | 0.35 | 17.5 |
| 5.4 | 0.5 (Example 4) | 12.5 | 12.5 | 3.9 | 0.82 | 0.31 | 17.5 |
| 9.4 (Reference Example 6) | 1.6 (Example 1) | 14.0 | 12.6 | 3.3 | 0.77 | 0.21 | 16.9 |
| 13.1 | 2.8 (Example 4) | 14.8 | 12.9 | 3.0 | 0.31 | 0.13 | 16.3 |
| 16.3 | 4.8 (Example 4) | 15.2 | 13.2 | 2.5 | 0.11 | 0.05 | 15.9 |
| 24.2 | 7.2 (Example 4) | 18.9 | 9.5 | 1.6 | Undetectable | Undetectable | 11.1 |
| 30.0 | 9.3 (Example 4) | 21.1 | 8.0 | 0.96 | Undetectable | Undetectable | 9.0 |

INDUSTRIAL APPLICABILITY

In the method of producing a sugar liquid and a xylooligosaccharide, a filamentous fungus-derived cellulase used for production of a sugar liquid from a cellulose-containing biomass is recovered, and then it is reused in production of a xylooligosaccharide. Therefore, the production cost of the xylooligosaccharide can be reduced. The sugar liquid produced can be used as a fermentation feedstock for various kinds of chemical products. The xylooligosaccharide produced can be used as an additive for foods and feeds.

The invention claimed is:

1. A method of producing a xylooligosaccharide, comprising Steps (1) to (3):
   Step (1): hydrolyzing a cellulose-containing biomass with a filamentous fungus-derived cellulase having xylanase activity and β-xylosidase activity;
   Step (2): subjecting the hydrolysate of Step (1) to solid-liquid separation, and filtering the solution component through an ultrafiltration membrane to recover cellulase as a non-permeate; and
   Step (3): reacting the recovered cellulase in Step (2) with a xylan-containing material, and recovering a xylooligosaccharide produced, Step (3) being independent from Step (1),
   wherein, in Step (2), electric conductivity of the hydrolysate in Step (1) is less than 16 mS/cm.

2. The method according to claim 1, wherein said filamentous fungus-derived cellulase is *Trichoderma reesei*-derived cellulase.

3. The method according to claim 1, wherein the β-xylosidase activity of the recovered cellulase in Step (2) is less than 5% of that of the filamentous fungus-derived cellulase used in Step (1).

4. The method according to claim 1, wherein the recovered cellulase in Step (2) contains at least xylanase.

5. The method according to claim 1, wherein Step (1) is a step of hydrolyzing a pretreated product of the cellulose-containing biomass with the filamentous fungus-derived cellulase.

6. The method according to claim 5, wherein Step (1) is a step of hydrolyzing, with the filamentous fungus-derived cellulase, a product obtained by washing a solid component contained in the pretreated product of the cellulose-containing biomass with water.

7. The method according to claim 1, wherein the xylan-containing material is a pretreated product of a cellulose-containing biomass.

8. The method according to claim 7, wherein the xylan-containing material is a solution component obtained by solid-liquid separation of the pretreated product of the cellulose-containing biomass.

9. The method according to claim 7, wherein the xylan-containing material is a solid component obtained by solid-liquid separation of the pretreated product of the cellulose-containing biomass.

10. The method according to claim 9, further comprising repeating Steps (1) to (3), wherein a hydrolysis residue obtained in Step (3) is used as part or all of the cellulose-containing biomass in Step (1) in the repeated steps.

11. The method according to claim 1, further comprising recovering a sugar liquid as a permeate in Step (2).

* * * * *